(12) United States Patent  
Sivard et al.

(10) Patent No.: US 8,437,863 B2
(45) Date of Patent: May 7, 2013

(54) ELECTRODE LEAD

(75) Inventors: Åke Sivard, Solna (SE); Gustav Pellijeff, Årsta (SE); Hans Strandberg, Sundbyberg (SE); Leda Henriquez, Vällingby (SE); Åsa Broomé, Hässelby (SE); Kenneth Dahlberg, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 164 days.

(21) Appl. No.: 13/140,729

(22) PCT Filed: Dec. 19, 2008

(86) PCT No.: PCT/SE2008/000728
§ 371 (c)(1),
(2), (4) Date: Jun. 17, 2011

(87) PCT Pub. No.: WO2010/071493
PCT Pub. Date: Jun. 24, 2010

(65) Prior Publication Data
US 2011/0251654 A1   Oct. 13, 2011

(51) Int. Cl.
*A61N 1/05* (2006.01)
(52) U.S. Cl.
USPC .............................. 607/115; 607/18; 607/122
(58) Field of Classification Search .................. 607/2, 9, 607/18, 27, 29, 30, 115–119, 122
See application file for complete search history.

(56) References Cited

U.S. PATENT DOCUMENTS

| | | | |
|---|---|---|---|
| 5,843,135 A | 12/1998 | Weijand et al. | |
| 6,795,730 B2 | 9/2004 | Connelly et al. | |
| 6,819,954 B2 | 11/2004 | Connelly | |
| 7,082,328 B2 | 7/2006 | Funke | |
| 7,123,013 B2 | 10/2006 | Gray | |
| 7,363,090 B2 | 4/2008 | Halperin et al. | |
| 7,369,898 B1 | 5/2008 | Kroll et al. | |
| 2002/0116028 A1 | 8/2002 | Greatbatch et al. | |
| 2002/0116029 A1 | 8/2002 | Miller et al. | |
| 2002/0116033 A1 | 8/2002 | Greatbatch et al. | |
| 2002/0116034 A1 | 8/2002 | Miller et al. | |
| 2003/0088303 A1 | 5/2003 | Goode | |
| 2003/0204217 A1 | 10/2003 | Greatbatch | |
| 2004/0088012 A1 | 5/2004 | Kroll et al. | |

(Continued)

FOREIGN PATENT DOCUMENTS
WO       WO 99/43381       9/1999

*Primary Examiner* — Brian T Gedeon

(57) ABSTRACT

An implantable electrode lead for tissue stimulation adapted to be attached to an implantable tissue stimulator provided with a pulse generator, has at least two stimulation electrodes to apply stimulation pulses to said tissue and arranged close to the distal end of the electrode lead, and at least two electrical conductors to connect said electrodes to said pulse generator. The electrode lead further has a switching unit arranged close to the distal end of the electrode lead and adapted to switch the electrode lead between a local pacing mode and a normal pacing mode, the switching unit being controlled by a mode control signal. Further, a pacing module is arranged close to the distal end of the electrode lead and in relation to the switching unit and being connectable to said at least two stimulation electrodes, the pacing module includes a pulse generating unit to generate stimulating pulses to be applied to the tissue by the stimulation electrodes. When the electrode lead is in the local pacing mode the electrical conductors are disconnected from said stimulation electrodes which instead are connected to the pacing module, and when the electrode lead is in the normal pacing mode the electrical conductors are connected to the stimulation electrodes.

15 Claims, 3 Drawing Sheets

U.S. PATENT DOCUMENTS

| | | |
|---|---|---|
| 2006/0142813 A1 | 6/2006 | Maschke |
| 2006/0167496 A1 | 7/2006 | Nelson et al. |
| 2007/0238975 A1 | 10/2007 | Zeijlemaker |
| 2008/0079429 A1 | 4/2008 | Gray |
| 2008/0154342 A1 | 6/2008 | Digby et al. |
| 2008/0154348 A1 | 6/2008 | Atalar et al. |
| 2009/0149906 A1 | 6/2009 | Ameri et al. |
| 2009/0149909 A1 | 6/2009 | Ameri |

ELECTRODE LEAD

BACKGROUND OF THE INVENTION

1. Field of the Invention

The present invention concerns an implantable medical lead for tissue stimulation of the type that is adapted to be attached to an implantable tissue stimulator that includes a pulse generator, the electrode lead being of the type having at least two stimulation electrodes to apply stimulation pulses to the tissue, with the stimulation electrodes being located close to the distal end of the electrode lead, and the electrode lead having at least two electrical conductors that electrically connect the electrodes to the pulse generator.

2. Description of the Prior Art

Implantable pulse generator (IPG) systems are considered contraindicative to Magnetic Resonance Imaging (MRI). One concern discussed regarding compatibility of IPG systems and MRI scanning is heating at or close to the lead tip, caused by currents in the lead induced by the applied RF-field from the MRI system, i.e. the IPG lead is acting as an antenna picking up the RF field during the MRI scan.

If the heating is too high, there is a concern that there may be damages to the cardiac tissue.

The use of MRI scans for diagnostics is growing extensively and an increasing, already large number of IPG patients would benefit from MRI scans. It is thus desirable to reduce any heating at or close to the lead tip to acceptable and safe levels.

In the prior art a number of patents and patent applications exist related to different solutions of the above problem with MRI-scanning of IPG patients.

The solutions proposed in the prior art may be divided into two main groups.

The first group is essentially based upon filtering, insulating or compensation techniques to reduce effects of MRI.

U.S. Pat. No. 7,363,090, for example, includes a band stop filter arranged to attenuate a current flow through the lead wire along a range of selected frequencies.

In U.S. Pat. No. 7,123,013 a tuneable compensation circuit is connected to the lead wire line. This circuit applies supplemental impedance to the wire line to cause the characteristic impedance of the wire line to become unbalanced, thereby reducing the effects of induced voltages caused by the MRI field.

In US-2003/0204217 an electrode isolation system electrically isolates the lead electrodes from the voltage discharge unit during time intervals between the voltage pulses.

In US-2007/0238975 an MRI gradient magnetic field is sensed and the system switches from a first electrical signal processing mode to a second electrical signal processing mode based upon the sensed field.

US-2008/0079429 relates to an implantable medical device with two medical leads and a filter circuit coupled to the distal end of the first lead. A compensation circuit provides compensation voltage to enable the filter to effectively block changing magnetic field induced current in the second lead from passing through a second electrode of the distal end of the second lead.

In the second group, represented by US-2002/0116028, so-called photonic leads or catheters are used where electrical pulses output by the pulse generator are converted into light energy and directed into the proximal end of the photonic catheter. The photonic catheter includes an optical conduction pathway and light entering the proximal end of the catheter is transmitted through the optical pathway, where it is collected and converted back to electrical energy at the distal end of the photonic catheter. The optical pulses are then converted to electrical pulses and delivered to the heart electrodes.

In US-2002/0116029 a similar system is disclosed, differing in that a miniature pulse generator is arranged at the distal end of the photonic catheter that stores electrical energy received via the optical conductors and periodically releases that energy to deliver electrical pulses to the bipolar heart electrodes. A similar device is also disclosed in US-2002/0116034.

SUMMARY OF THE INVENTION

An object of the present invention is to solve the problem of heat generation induced by the magnetic fields when performing MRI of a patient having an implantable heart stimulator.

A more general object of the present invention is to achieve an alternative stimulation mode in situations where the normal pacing mode of the implantable heart stimulator may not be possible or suitable to use.

Thus, the present invention solves the above problem by disconnecting the stimulating electrodes, e.g. the tip and the ring, from the rest of the lead (i.e. antenna) during MRI, or when another predefined situation occurs that motivates use of the local pacing mode. According to the invention a pacing module is arranged close to the distal tip. In addition a switching unit is arranged close to the pacing module that during the normal pacing mode is closed, i.e. the stimulating electrodes are connected to the pulse generator of the heart stimulator. When the heart stimulator is put in local pacing mode (MRI mode) the tip and ring are disconnected from the rest of the lead, and the heart stimulator, and instead connected to the pacing module. The pacing module includes a very simple pacemaker function that takes care of the pacemaker functionality during the MRI scan.

According to one embodiment of the present invention the local stimulation rate is set, during MRI, at an appropriate overdrive rate if the patient's intrinsic rate is low/none-existent. If the patient's intrinsic rate is sufficient the switching unit only disconnects the electrical conductors from the stimulation electrodes.

According to another embodiment the local pacing module and the switching unit is energised by an energy unit being a battery or a capacitor, or by energy supplying conductors going through the lead all the way up to the heart stimulator battery. These conductors are not directly connected to the tip and/or the ring so there is no problem if voltage is induced in them during MRI and they are heated. I.e. the thin conductors are connected to the tip and/or ring via the pacing module and switching unit close to the tip of the lead and thus not directly connected to the tip/ring.

DESCRIPTION OF THE PREFERRED EMBODIMENTS

Figure 1:
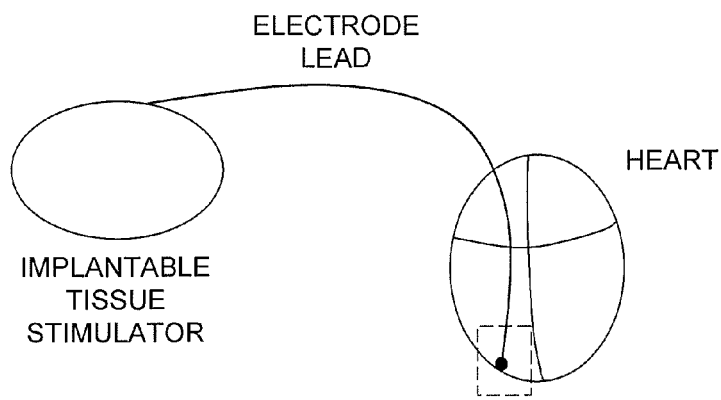
FIG. 1 is a schematic illustration of an implantable tissue stimulator provided with an electrode lead according to the present invention.

With reference to FIG. 1 the present invention relates to an implantable electrode lead for tissue stimulation adapted to be attached to an implantable tissue stimulator provided with a pulse generator (not shown). The electrode lead comprises at least two stimulation electrodes to apply stimulation pulses to the tissue and arranged close to the distal end of the electrode lead, and at least two electrical conductors (not shown) to connect the electrodes to the pulse generator.

Figure 2:
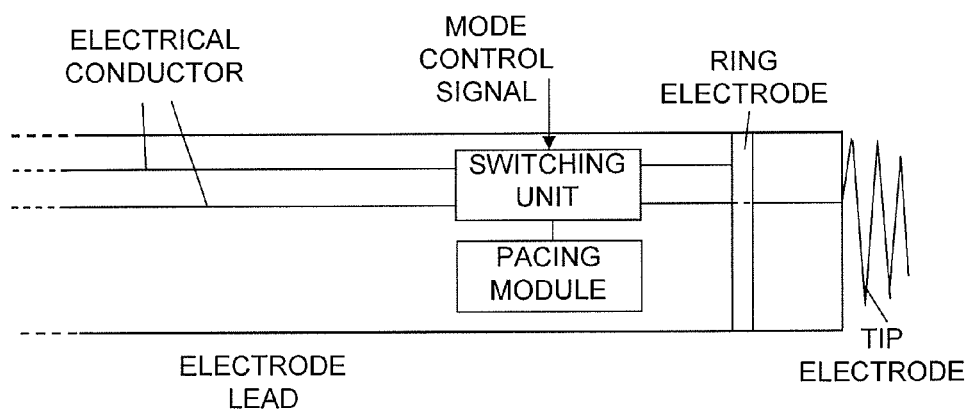
FIG. 2 shows a schematic illustration of the distal part of an electrode lead according to the present invention.

In FIG. 2 the distal end of the electrode lead is schematically illustrated. The electrode lead comprises a switching unit arranged close to the distal end of the electrode lead and adapted to switch the electrode lead between a local pacing mode configuration and a normal pacing mode configuration. The switching unit being controlled by a mode control signal. The electrode lead further comprises a pacing module arranged close to the distal end of the electrode lead and in relation to the switching unit and being connectable to the at least two stimulation electrodes. The pacing module includes a pulse generating unit to generate stimulating pulses to be applied to the tissue by the stimulation electrodes.

When the electrode lead is in the local pacing mode the electrical conductors are disconnected, by the switching unit, from the stimulation electrodes which instead are connected to the pacing module, and when the electrode lead is in the normal pacing mode the electrical conductors are connected to the stimulation electrodes.

Figure 3:
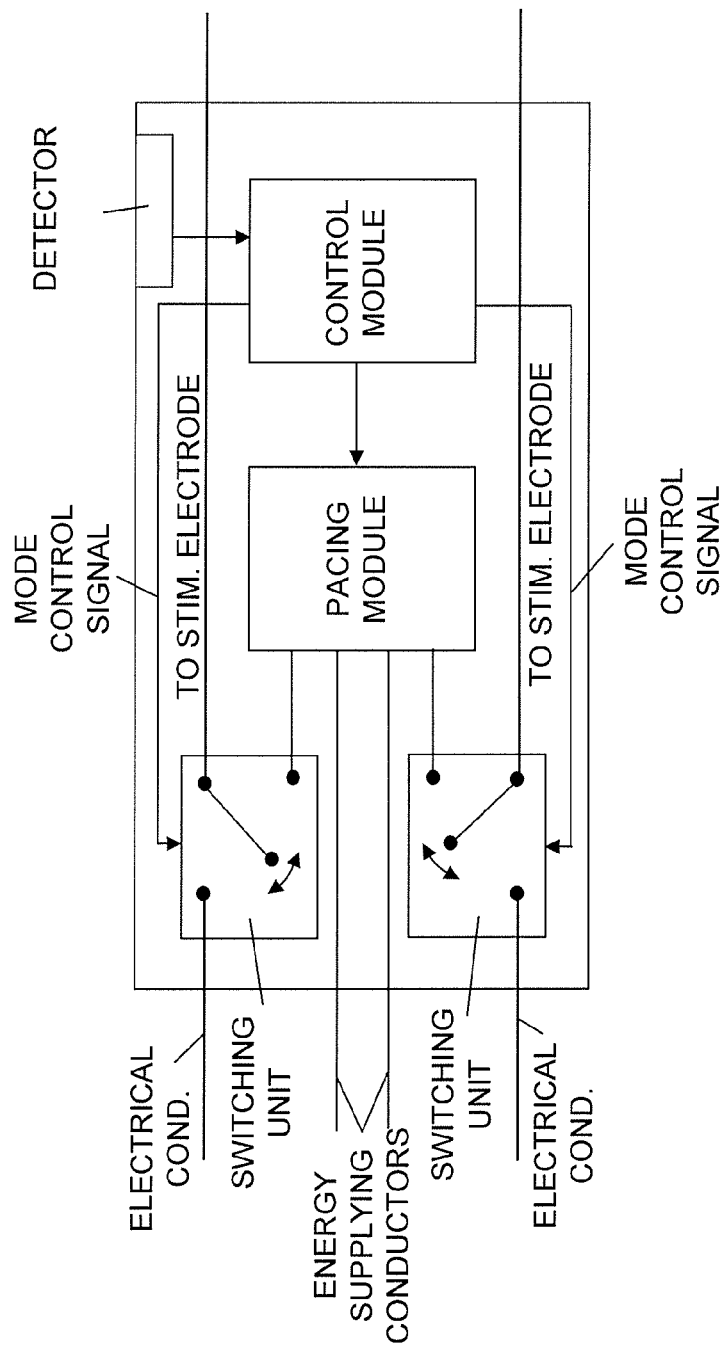
FIG. 3 shows a schematic illustration of the distal part of an electrode lead according to a preferred embodiment of the present invention.

According to a preferred embodiment, which is illustrated by the schematic block diagram in FIG. 3, the electrode lead further comprises a control module arranged close to the distal end of the lead and in relation to the switching unit, the control module is adapted to generate the mode control signal.

According to an embodiment of the present invention the local pacing mode is applicable when certain predefined criteria are fulfilled and the mode control signal is generated in dependence thereto.

According to a preferred embodiment the mode control signal is generated by the implantable tissue stimulator and supplied to the switching unit via an electrical connection in the electrode lead. In this case the normal situation is probably that the tissue stimulator has received information via telemetry that the local pacing mode should be applied because an MRI scan is to be performed.

According to a preferred embodiment the electrode lead further comprises a magnetic resonance (MR) detector, which is schematically illustrated in FIG. 3, adapted to detect a magnetic resonance (MR) field of predetermined field strength, and in response of such detection to generate the mode control signal. The predetermined field strength is 0.1 Tesla or higher.

Preferably, the MR detector is a Hall element sensor. As an alternative the MR detector is a Giant Magnetic Resistance (GMR) sensor.

According to another preferred embodiment the electrode lead comprises a radio frequency (RF) sensor adapted to detect a radio frequency field of predetermined field strength, and in response of such detection generate the mode control signal.

According to still another predetermined embodiment the electrode lead comprises a temperature sensor adapted to detect an increased temperature in the distal end of the lead, and in response of such detection generate the mode control signal.

The electrode lead further includes an energy unit, e.g. a battery or a capacitor, arranged close to the distal end of the lead and used to energize the switching unit and pacing module.

The required energy needed for the circuitry in the distal end of the electrode lead, the pacing module, the switching unit, and other optional circuitry may as an alternative be supplied via energy supplying conductors arranged in the electrode lead. These conductors are connected to the implantable tissue stimulator.

Preferably, when the electrode lead is in the local pacing mode the electrodes are also used to sense heart events.

The stimulating pulses generated by the pacing module, during the local pacing mode, may be varied with regard to stimulation rate and stimulation energy as will be further outlined in the following, and when discussing FIG. 4.

According to one preferred embodiment, when in the local pacing mode, the pacing module generates stimulating pulses at a fixed rate being the stimulation rate used in the normal pacing mode prior switching to the local pacing mode. As an alternative, the fixed rate is set to a specific value, e.g. 70 or 80 stimulations per minute.

As a further alternative, when in the local pacing mode, the pacing module generates stimulating pulses at a variable rate starting at the stimulation rate used in the normal pacing mode prior switching to the local pacing mode and then varied in dependence of sensed heart events.

During normal pacing mode (no MRI scan) the switching unit connect the respective electrical conductor to the connection to the stimulation electrodes which in FIG. 3 is achieved by setting the switching unit in the horizontal direction.

For safety reasons this connection is maintained if the available energy, e.g. the battery, for the pacing module is too low.

Before or at the start of an MRI scan the pacemaker system goes into the local pacing mode, either automatically, e.g. a sensed RF-field detected by detector initiates mode change, or via programming from an external programming device. During MRI mode the switching unit instead connect the pacing module to the respective stimulation electrodes.

In FIG. 3 the mode control signal is generated by the control module. As an alternative the mode control signal is generated by the tissue stimulator, lead to the distal end of the electrode lead via a thin wire (not shown) and applied to the switching unit.

In the local pacing mode only a small part of the lead is connected to the stimulating electrodes resulting in an insignificant heating of the parts of the lead connected to the tissue/blood (tip and ring).

For a pacemaker dependent patient (very low or non-existent intrinsic heart rate) the pacing module now takes over the pacing of the patient. This can for instance be done in the following way. The pacing module includes an oscillator that generates a clock signal to a charge pump in the pacing module where the programmed pace pulse amplitude is generated over an output capacitor. The pacing module then signals to the output stage to put out a pace pulse by connecting the output capacitor to the stimulating electrodes. Preferably, the output capacitor has a capacitance in the range of $\mu F$. Today there are 4.7 $\mu F$ capacitors available in 1.6×0.8 mm size (or even smaller) on the market.

If the patient has a sufficient intrinsic rate no pacing is needed and it is enough to disconnect the electrical conductors of the electrode lead from the tissue stimulator via the switching unit.

Figure 4:
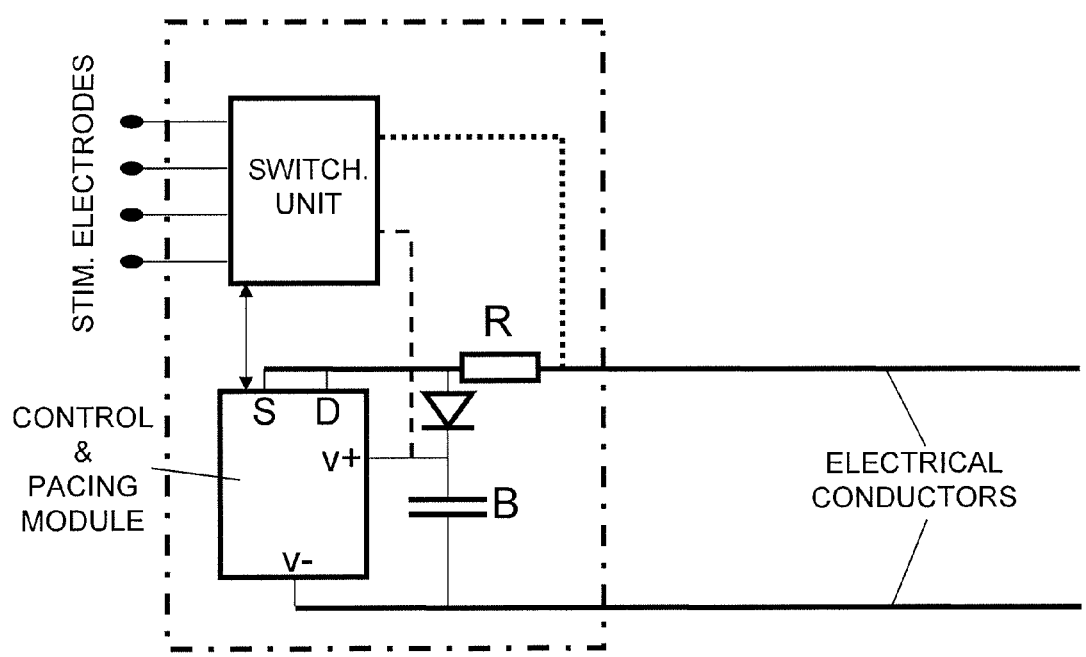
FIG. 4 shows a schematic illustration of the distal part of an electrode lead according to another preferred embodiment of the present invention.

FIG. 4 illustrates a schematic block diagram of still another embodiment of the present invention.

In this embodiment four stimulation electrodes are included, being e.g. tip-electrodes, ring electrodes, and/or coronary sinus electrodes.

The electrical conductors are connected to an implantable tissue stimulator (not shown) responsible for pulse generation during the normal pacing mode. In that mode the switching unit is switched such that the stimulation electrodes receive stimulation energy from the tissue stimulator via the dotted line.

When the electrode lead is set to work in the local pacing mode the switching unit is switched such that the stimulation electrodes receive, via the dashed line, stimulation energy from the local energy unit B, being e.g. a battery, a capacitor having large capacitance, or a "super-capacitor". The requirements of the local energy unit B is that it can generate the required energy during a minimum time period, e.g. related to the time it takes to perform an MRI procedure.

According to this embodiment a resistor R is arranged at one of the electrical conductors close to the tip circuitry. The resistor has a resistance of 2-20 kOhm to limit current induced by RF. The voltage drop is then minimized for currents in the interval of 1-20 µA, while RF is effectively suppressed.

In this embodiment the switching unit has two purposes, the first is to ensure switching between the normal and local pacing mode and the second is to control between which of electrodes the stimulation pulse is applied.

The bi-directional arrow between the switching unit and the control and pacing module indicates a system of communication channels for control signals to control the switching unit, and to receive sensed heart signals.

In the following the mode control will be further discussed.

When the electrode lead is in the normal pacing mode the control unit of the heart stimulator passively stores information regarding stimulation rate, sensed heart activity etc.

According to a preferred embodiment the mode control is different dependent upon where the electrode lead is positioned. During implantation it is set, preferably in the control unit, the position of the electrode lead, e.g. if it is positioned in the atrium, ventricle or in the coronary sinus.

Preferably, if the electrode lead is positioned in the atrium no local pacing mode is available; instead the switching unit only disconnects the electrodes from the electrical conductors without connecting them to the pacing module.

If the electrode lead is positioned in the ventricle a number of different situations must be analyzed prior the local pacing mode is applied.

The analysis is based upon measured stimulation pulse interval lengths in an undisturbed environment. These are measured by a control unit of the heart stimulator.

In addition normal heart sensing is performed by the heart stimulator. The stimulation pulse interval lengths and marker pulses representing sensed heart events are communicated to the control module at the electrode lead tip.

In the following four essentially different situations are described resulting in different therapy modes.

1) Only stimulation pulses and no sensed heart events are detected. The stimulation interval length may have a preset interval length or may be varied in the dependence of a rate responsive function.

In the local pacing mode a preset stimulation rate is then used. The preset stimulation rate may be the last measured rate or a previous rate that may be slightly higher, but the normal rate is preferred, e.g. 70 pulses/min. Preferably, the stimulation pulses are set to a slightly higher amplitude than during normal stimulation.

2) Intrinsic heart events occur frequently, with no stimulation pulses. If some stimulation pulses occur, there are never two consecutive pulses. In this case the local pacing mode is not activated.

3) Stimulation pulses and heart events occur together, having intervals never shorter than a measured minimum value. The measured minimum interval must not be physiologically inadequate, e.g. must not be shorter than the interval length that corresponds to 110/min, or a preset threshold value adapted to the patient.

The local pacing module then stimulates in an overdrive mode, i.e. uses set stimulation rate with an interval length slightly shorter than the measured minimum value. As in the first case the stimulation pulses may have slightly higher amplitude than during normal stimulation.

4) Stimulation pulses and heart events occur together having measured intervals where the shortest intervals are too short, e.g. shorter than a preset proportion of the corresponding length interval of the maximum tracking rate (MTR). The control unit of the heart stimulator must then further analyse the situation and prepare communication information via telemetry to the external programmer that no safe stimulation mode exists.

A decision regarding relevant therapy must then be taken of a physician having all information of the patient's status.

The recommendation is then based upon some of, or all of the following items a-d:

a) give a rate reducing heart drug, b) give an arrhythmia controlling drug, c) apply a relevant overdrive stimulation rate, d) a physician performs constant monitoring of the patient's ECG in relation to the functionality of the implanted heart stimulator.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable electrode lead comprising:
    a lead body adapted for in vivo implantation in a subject, said lead body having a distal portion terminating in a distal end, and a proximal end opposite to said distal end;
    said proximal end being configured to connect said proximal end to an implantable tissue stimulator that comprises a pulse generator that is configured to emit stimulation pulses;
    at least two electrical conductors inside said lead body and adapted for connection via said proximal end to said pulse generator of said implantable tissue stimulator;
    at least two stimulation electrodes located at said distal portion of said electrode lead and respectively electrically connected to said at least two electrical conductors;
    a pacing module located at said distal portion of said lead body, said pacing module comprising a pacing module pulse generating unit that is configured to generate stimulation pulses; and
    a switching unit located at said distal portion of said lead body and having a mode control input, said switching unit being configured, in response to a mode control signal received via said mode control input, to switch between a local pacing mode and a normal pacing mode and, in said normal pacing mode, to maintain said electrical conductors connected to said stimulation electrodes and, in said local pacing mode, to disconnect said stimulation electrodes from said electrical conductors and to connect said stimulation electrodes to said pacing module pulse generating unit to supply said stimulation pulses from said pacing module pulse generating unit to said stimulation electrodes.

2. An implantable electrode lead as claimed in claim 1 comprising a control module located at said distal portion of said lead body and being in communication with said switching unit to supply said mode control signal thereto.

3. An implantable electrode lead as claimed in claim 1 wherein said control module is configured to identify when a predetermined criterion exists and to generate said mode control signal when said predetermined criterion exists.

4. An implantable electrode lead as claimed in claim 1 wherein a source of said mode control signal is located in said implantable tissue stimulator, and wherein said implantable electrode lead comprises an electrical connection via said proximal end to said switching unit via which said mode control signal is supplied to said switching unit.

5. An implantable electrode lead as claimed in claim 1 comprising a magnetic resonance detector configured to detect a magnetic resonance field of a predetermined field strength, said magnetic resonance detector being connected to said mode control input of said switching unit and supplying said mode control signal to said switching unit upon detection of said magnetic resonance field of said predetermined field strength.

6. An implantable electrode lead as claimed in claim 5 wherein said predetermined field strength is 0.1 Tesla or higher.

7. An implantable electrode lead as claimed in claim 5 wherein said magnetic resonance detector is a Hall element sensor.

8. An implantable electrode lead as claimed in claim 5 wherein said magnetic resonance detector is a giant magnetic resistance sensor.

9. An implantable electrode lead as claimed in claim 1 comprising a radio-frequency sensor configured to detect a radio-frequency field of a predetermined field strength, said radio-frequency sensor being connected to said mode control input of said switching unit and supplying said mode control signal to said switching unit upon detection of said radio-frequency field of said predetermined field strength.

10. An implantable electrode lead as claimed in claim 1 comprising a temperature sensor configured to detect an increase in temperature at said distal end of said lead body, said temperature sensor being connected to said mode control input of said switching unit and supplying said mode control signal to said switching unit upon detection of said increased temperature at said distal end of said lead body.

11. An implantable electrode lead as claimed in claim 1 comprising an energy source at said distal portion of said lead body connected to said switching unit and to said pacing module to supply energy to operate said switching unit and said pacing module.

12. An implantable electrode lead as claimed in claim 1 comprising energy supplying conductors in said lead body and respectively connected to said proximal end of said lead body and to said switching unit and said pacing module, and wherein said implantable tissue stimulator comprises an energy source and wherein said proximal end of said lead body is adapted to connect said energy supplying conductors to said energy source.

13. An implantable electrode lead as claimed in claim 1 wherein said pacing module is configured to identify a pacing rate that occurs in said normal pacing mode and to operate said pulse generating unit of said pacing module in said local pacing mode to emit stimulation pulses at a pacing rate occurring in said normal pacing mode prior to switching to said local pacing mode.

14. An implantable electrode lead as claimed in claim 1 wherein said stimulation electrodes, when said switching unit is in said local pacing mode, are also configured to sense cardiac events.

15. An implantable electrode lead as claimed in claim 14 wherein said pacing module is configured to operate said pulse generating unit of said pacing module at a variable pacing rate in said local pacing mode dependent on the cardiac events sensed by said stimulation electrodes.

* * * * *